US007796255B2

United States Patent
Miller

(10) Patent No.: US 7,796,255 B2
(45) Date of Patent: Sep. 14, 2010

(54) OPTICAL PARTICLE SENSOR WITH EXHAUST-COOLED OPTICAL SOURCE

(75) Inventor: Rick Miller, Loveland, CO (US)

(73) Assignee: Particle Measuring Systems, Inc., Boulder, CO (US)

(*) Notice: Subject to any disclaimer, the term of this patent is extended or adjusted under 35 U.S.C. 154(b) by 313 days.

(21) Appl. No.: 12/052,923

(22) Filed: Mar. 21, 2008

(65) Prior Publication Data

US 2008/0246965 A1 Oct. 9, 2008

Related U.S. Application Data

(60) Provisional application No. 60/896,649, filed on Mar. 23, 2007.

(51) Int. Cl.
 *G01N 21/00* (2006.01)
 *G01N 1/10* (2006.01)
(52) U.S. Cl. ............... 356/337; 356/246; 356/432; 422/83
(58) Field of Classification Search ......... 356/432–444, 356/246, 336–339, 319; 250/458.1, 461 R, 250/343; 422/73, 82–83
 See application file for complete search history.

(56) References Cited

U.S. PATENT DOCUMENTS

| | | | |
|---|---|---|---|
| 3,941,982 A | | 3/1976 | Knollenberg et al. |
| 4,011,459 A | | 3/1977 | Knollenberg et al. |
| 4,027,162 A | | 5/1977 | Knollenberg |
| 4,180,739 A | * | 12/1979 | Abu-Shumays .......... 250/461.1 |
| 4,571,079 A | | 2/1986 | Knollenberg |
| 4,594,715 A | | 6/1986 | Knollenberg |
| 4,636,075 A | | 1/1987 | Knollenberg |
| 4,728,190 A | | 3/1988 | Knollenberg |
| 4,739,467 A | * | 4/1988 | Furusawa .................... 700/28 |
| 4,740,988 A | | 4/1988 | Knollenberg et al. |
| 4,764,086 A | | 8/1988 | Jesinger |

(Continued)

FOREIGN PATENT DOCUMENTS

WO WO 02/065595 8/2002

(Continued)

OTHER PUBLICATIONS

International Search Report, Corresponding to International Application No. PCT/US2008/057787, Mailed Jul. 17, 2008.

(Continued)

*Primary Examiner*—Sang Nguyen
(74) *Attorney, Agent, or Firm*—Greenlee Sullivan P.C.

(57) ABSTRACT

The invention relates to particle sensors that are capable of passively cooling high-powered optical sources within the sensor, thereby extending the optical source lifetime without requiring additional power. The sensor detects particles within a sample fluid by optical interaction of the optical source with flowing sample fluid in the sample chamber. Sample fluid that exits the sample chamber is directed into thermal contact with the optical source, thereby cooling the optical source. Sample fluid that has come into thermal contact with the optical source is continuously removed from the sensor to ensure the optical source is adequately cooled. A variety of elements are used to facilitate thermal contact between the optical source and sample fluid including plenums, heat sinks, and airflow cavities. Provided are related methods for cooling a one or more heat-producing device within a particle sensor.

46 Claims, 10 Drawing Sheets

U.S. PATENT DOCUMENTS

| | | | |
|---|---|---|---|
| 4,798,465 A | 1/1989 | Knollenberg | |
| 4,871,251 A | 10/1989 | Preikschat et al. | |
| 4,893,928 A | 1/1990 | Knollenberg | |
| 4,893,932 A | 1/1990 | Knollenberg | |
| 5,029,335 A | 7/1991 | Fisher et al. | |
| 5,085,500 A | 2/1992 | Blesener et al. | |
| 5,099,311 A | 3/1992 | Bonde et al. | |
| 5,134,622 A | 7/1992 | Deacon | |
| 5,282,151 A | 1/1994 | Knollenberg | |
| 5,459,569 A | 10/1995 | Knollenberg et al. | |
| 5,493,123 A | 2/1996 | Knollenberg et al. | |
| 5,671,046 A | 9/1997 | Knowlton | |
| 5,740,018 A | 4/1998 | Rhumbut | |
| 5,751,422 A | 5/1998 | Mitchell | |
| 5,805,281 A | 9/1998 | Knowlton et al. | |
| 5,861,950 A | 1/1999 | Knowlton | |
| 5,875,206 A | 2/1999 | Chang | |
| 5,903,338 A | 5/1999 | Mavliev et al. | |
| 6,069,907 A | 5/2000 | Chang | |
| 6,091,494 A | 7/2000 | Kreikebaum | |
| 6,167,107 A | 12/2000 | Bates | |
| 6,246,474 B1 | 6/2001 | Cerni et al. | |
| 6,246,816 B1 | 6/2001 | Moore et al. | |
| 6,275,290 B1 | 8/2001 | Cerni et al. | |
| 6,315,955 B1 * | 11/2001 | Klein | 422/73 |
| 6,437,551 B1 * | 8/2002 | Krulevitch et al. | 324/71.1 |
| 6,438,208 B1 | 8/2002 | Koller | |
| 6,490,040 B1 | 12/2002 | Berthold et al. | |
| 6,615,679 B1 | 9/2003 | Knollenberg et al. | |
| 6,687,271 B2 | 2/2004 | Um et al. | |
| 6,690,696 B2 | 2/2004 | Byren et al. | |
| 6,709,311 B2 | 3/2004 | Cerni | |
| 6,717,665 B2 * | 4/2004 | Wagner et al. | 356/244 |
| 6,785,310 B2 | 8/2004 | Huber et al. | |
| 6,829,044 B2 * | 12/2004 | Liu | 356/37 |
| 6,859,277 B2 * | 2/2005 | Wagner et al. | 356/337 |
| 6,865,200 B2 | 3/2005 | Takigawa et al. | |
| 6,903,818 B2 | 6/2005 | Cerni et al. | |
| 6,945,090 B2 | 9/2005 | Rodier | |
| 7,030,980 B1 | 4/2006 | Sehler et al. | |
| 7,075,652 B1 * | 7/2006 | Sarvazyan et al. | 356/432 |
| 7,088,446 B2 | 8/2006 | Cerni | |
| 7,088,447 B1 | 8/2006 | Bates et al. | |
| 7,208,123 B2 * | 4/2007 | Knollenberg et al. | 422/83 |
| 7,576,857 B2 * | 8/2009 | Wagner | 356/337 |
| 2002/0110165 A1 | 8/2002 | Filgas | |
| 2002/0159207 A1 | 10/2002 | Zimmerman et al. | |
| 2003/0098421 A1 | 5/2003 | Ho | |
| 2005/0123011 A1 | 6/2005 | Sukhman et al. | |
| 2005/0152146 A1 | 7/2005 | Owen et al. | |
| 2005/0190557 A1 | 9/2005 | Zhan et al. | |
| 2006/0038998 A1 | 2/2006 | Wagner | |
| 2006/0274309 A1 | 12/2006 | Cerni et al. | |

FOREIGN PATENT DOCUMENTS

WO    WO 2004/061957    7/2004

OTHER PUBLICATIONS

Weisstein. Definition of a Reynolds Number. 1996-2007. Retrieved from the Internet, Jul. 11, 2008, http://scienceworl.wolfram.com/physics/ReynoldsNumber.html.

Written Opinion, Corresponding to International Application No. PCT/US2008/057787, Mailed Jul. 17, 2008.

* cited by examiner

OPTICAL PARTICLE SENSOR WITH EXHAUST-COOLED OPTICAL SOURCE

CROSS-REFERENCE TO RELATED APPLICATIONS

This application claims the benefit under 35 U.S.C. 119(e) of U.S. Provisional Patent Application No. 60/896,649 filed on Mar. 23, 2007.

BACKGROUND OF THE INVENTION

The invention is generally in the field of optical particle sensing and provides systems and methods for cooling optical sources used in optical particle sensors. The cooling systems of the present invention substantially increase the operating life of optical sources, such as a laser, within the sensor and are relatively inexpensive and simple to incorporate into an optical particle sensor.

Optical particle sensors and counters are useful in a variety of industrial applications where it is important that the purity of materials used in a process be continuously monitored. For example, in semi-conductor and other clean-room settings, or industries requiring sterile and pure production (e.g., pharmaceuticals), material fluids that are used to make the end product are continuously monitored to ensure adequate purity and that any unwanted particles suspended in the fluid is within an acceptable tolerance range. It is particularly advantageous to rapidly identify when a fluid is contaminated with unwanted particles so that the process can be stopped at an early stage, thereby avoiding wasteful manufacture of defective product.

The importance of particle monitoring sensors is reflected in the continuous and ongoing improvement and development of these devices to improve reliability and throughput and to enable detection and characterization of particles having smaller sizes. In particular, particle measuring devices and particle sensors are becoming more sophisticated, capable of detecting sub-micron particles at higher fluid sampling rates (e.g., 1 CFM and higher). This improvement is at least partly a result of incorporation of more powerful optical sources such as laser diodes and diode arrays capable of delivering high radiant powers to samples subject to analysis. Optical sources that illuminate samples with high radiant power also, however, generate a substantial amount of heat. Studies indicate that laser operating life doubles for about every 10° C. drop in operating temperature. Accordingly, it is vital that optical particle counters with high energy optical sources be thermally managed in a manner compatible with clean room manufacturing processes. Prolonging optical source lifetime provides cost-savings beyond simply avoiding optical source replacement. Longer optical source lifetime increases process reliability and decreases process downtime. These advantages arise by avoiding unnecessary calibration that is required when an optical source within the sensor is replaced, or the entire sensor replaced. In addition, effective cooling of optical sources in particle counters provides a more reliable light output, thereby reducing noise and enhancing detection. The thermal management and control of the present invention results in improved measuring device capabilities and reliability.

Cooling mechanisms commonly used for optical sources in particle counters include active thermoelectric cooling which often require a substantial amount of power. For example, for a particle sensor requiring 13 W of energy to deliver 1.6 W of laser power from a laser diode, about 7 W of the 13 W total is for cooling the laser to a 20° C. delta temperature (US Pat. Pub. 2006/0038998). Although sample fluid has been used to cool an aperture element associated with the optical communication between the optical source and sample within a sample chamber (U.S. Pat. Pub. 2006/0038998), flow of exhaust sample fluid has not been used to directly cool an optical source. Other strategies for controlling the temperature of optical sources in optical particle sensors includes the use of a variety of device components that are separate from the exhaust fluid, including by heat sinks, powered cooling systems (U.S. Pat. Nos. 6,690,696; 6,091,494; 5,134,622) and forced air systems (U.S. Pat. No. 5,029,335).

Another need in the art relates to particle measuring devices that are associated with certain manufacturing processes common in clean room manufacturing and high-purity settings (e.g., semi-conductor or pharmaceutical manufacture). Such clean rooms require minimum case openings to ensure that access to the measurement instrument does not constitute a significant source of contaminants to the monitored environment. In addition, minimizing case openings facilitates easier biological cleaning and room decontamination, including cleaning and decontamination of the particle sensor. Accordingly, standard cooling techniques such as enclosure fans are inappropriate for these applications. The invention addresses the need in the art for cooling mechanisms that are capable of supplying adequate cooling and are not prone to these contamination issues.

The problem of heat generation by an optical source is generally recognized (e.g., U.S. Pat. Nos. 6,091,494; 5,029,335; 6,690,696), and accordingly heat dissipating means are generally provided with such optical sources. The available solutions, however, suffer from one or more limitations of complexity, expense, undesirable additional energy requirements, or are incompatible with the particle sensors of the present invention. Although particle sensors may have some residual cooling attributed to the fact that relatively cool sample fluid flows through the sample chamber that interacts with the optical source, they suffer from the limitation of not being able to adequately cool the optical source. Accordingly, those sensors generally require an active cooling mechanism to avoid excessive optical source operating temperature.

As will be understood from the forgoing description, optical particle sensors having thermally controlled optical sources are needed, particularly optical particle sensor having cooled optical sources exhibiting enhanced operating lifetimes. An additional need is for systems for providing thermal control of these sensors that do not require substantial additional power input. Furthermore, the thermal control in these sensing systems should be readily incorporated into optical particle sensors currently in use without a need for unduly excessive additional design and expense.

SUMMARY OF THE INVENTION

The present invention provides systems and methods for cooling one or more heat-producing elements within an optical particle sensor or sensing system. Methods and systems of the present invention use exhausted sample fluid conducted through regions of the optical particle sensor to provide effective thermal management, such as cooling, of selected device components. In some embodiments, for example, exhaust from an optical particle sensor is brought into thermal contact with a heat-producing element, such as an optical source. Transfer of thermal energy to the exhaust flow is used in the present invention to cool selected heat generating device components so as to reduce their operating temperature, thereby enhancing operating lifetime and performance of these components. The exhausted sample fluid in thermal contact with the heat producing element(s) is subsequently removed from the optical particle sensor so as to dissipate heat and provide thermal management of the sensing system.

Cooling strategies of the present invention utilize a temperature differential between the sample fluid introduced into a particle sensor and one or more heat-producing elements of the sensing system to provide targeted device component cooling. In particular, cooling of the heat-producing element is optionally passive, thereby minimizing or avoiding a need for active power-consuming cooling devices, such as thermoelectric cooling devices. Systems and methods of the present invention are particularly well suited for applications wherein low power consumption is advantageous, such as optical particle sensors that are part of a factory-integrated monitoring system, including sensors powered by a DC battery of low voltage and current.

Disclosed herein are basic particle sensor configurations combined with fluidic structures for cooling optical sources in sensor systems. In an embodiment, a flowing sample fluid is introduced into a sample chamber for optical analysis. After the sample has been optically analyzed in the sample chamber, sample fluid is removed and circulated along one or more specific fluidic pathways selected to establish thermal contact with a heat producing optical source element. In an aspect, substantially all the sample fluid is used to cool a heat-generating device. In another aspect, only a portion of the sample fluid is used to cool a heat-generating device, such as a portion of the sample fluid that is not required for cooling being exhausted to the environment. Alternatively, a first portion of sample fluid is directed to cool a first heat-generating device and a second portion of sample fluid is directed to cool a second heat-generating device. Alternatively, a plurality of heat-generating devices are cooled in series by a single flow-path of sample fluid such as essentially all the sample fluid or a portion of the sample fluid, as desired, depending on operating conditions and temperatures. Fluidic structures useful for establishing thermal contact include, but are not limited to, plenum chambers, air flow cavities, and optionally heat sink structures, or any combination thereof. Heat transfer provided by circulating exhausted sample fluid that is of a lower temperature than the temperature of the optical source provides cooling of the optical source without the need for any additional power or complex device configurations. Accordingly, the invention provides an elegant, versatile and reliable mechanism for maximizing optical source lifetime in a particle sensor by reducing operating temperatures.

In an embodiment, the invention provides an optical particle sensor system for sensing particles in a fluid sample. The sensor has a sample chamber with an inlet orifice for receiving a flow of fluid sample and an outlet orifice for conducting the fluid sample out of the sample chamber. As used herein, sample chamber refers to a component of the optical particle sensor where fluid sample is optically analyzed to characterize or detect particles within the fluid. The sensor includes an optical source that is in optical communication with the sample chamber. An outlet passage is provided in fluid communication with the outlet orifice of the sample chamber such that it receives flow of fluid sample exiting the sample chamber. Sample fluid that exits the sample chamber is referred to as exhaust sample fluid. The outlet passage is configured to have a portion in thermal contact with the optical source, thereby facilitating thermal exchange between the flow of sample fluid within the outlet passage and the optical source. This thermal exchange results in optical source cooling. Although the invention can be used to cool any heat-producing element, one major heat-producing element in these types of particle sensors is the optical source. In an aspect, the optical source or optical source is a high power optical source, such as a laser having a power consumption that is equal to or greater than about 100 mW, such as a laser optical source with an optical power in the range of 15 mW, corresponding to an energy requirement of about 150 mW. In another embodiment, the instrument is run at about 30-50 mW optical energy from a diode consuming about 300-500 mW of power.

During sensor operation, the optical source has an operating temperature. Thermal exchange between the flowing sample fluid in the outlet passage and the optical source results in optical source operating temperatures that are lower than a corresponding optical source operating temperature that is not in thermal contact with flowing sample fluid in an outlet passage. In an aspect, the flow of sample fluid in the outlet passage is capable of maintaining the operating temperature of the optical source to within about 5° C. of the fluid being sampled as compared to a 10° C. to 15° C. rise in the typical instrument internal temperature during operation of a device without sample fluid cooling. The cooling effect is even more pronounced in a common configuration where a remote sample may be 10° C. to 15° C. less than the ambient temperature surrounding the measurement instrument. Each 10° C. of additional temperature reduces the life of a laser diode by about 50%.

Because the magnitude of thermal transfer is related to the temperature differential between the two elements in thermal contact, an aspect of the invention is capable of being further described by a variety of temperature ranges at different locations throughout the sensor, sample fluid, and environment surrounding the sensor. In an aspect, the fluid sample at the sample chamber outlet has a temperature selected from a range of between about 20° C. and about 30° C. In an aspect, the temperature of the flowing sample fluid in the outlet passage, including the portion of the outlet passage in thermal contact with the optical source, is about of the same temperature as the fluid sample temperature in the sample chamber or fluid inlet, as there is very little dwell time between the inlet and this cooling area and therefore, minimal opportunity for the fluid to undergo a significant change in temperature.

The flow-rate of the sample fluid through the outlet passage is another parameter useful in the present systems and methods for providing effective cooling. The particular flow-rate depends on the characteristics of the system, including the geometry and dimensions of the portion in thermal contact, the heat capacity characteristics of the fluid, whether the fluid is liquid or gas, and the amount of heat dissipation required. Although the methods and systems of the present invention can utilize any flow-rate that provides adequate heat transfer for the particular application, in an aspect the outlet passage is capable of transmitting the flow of fluid sample at flow rates selected from the range of between about 25 L/min or 28.3 L/min (1 cfm) and 100 L/min.

Another physical parameter useful in the present systems and methods for optimizing heat exchange and cooling is the pressure of the flowing sample fluid in the portion of the outlet passage in thermal contact with the optical source. In an aspect, any of the sensors have a chamber pressure in the sample chamber and an outlet pressure in the outlet passage, wherein the chamber pressure and the outlet pressure are within about 10% of each other. In an aspect, the pressure drop in the outlet passage is minimized to control or minimize power consumption from the pump source.

In an aspect sensors of the present invention have a mounting element that supports the optical source, and specifically assists in reliably positioning the optical source with respect to the sample chamber. Because of the device geometry and connection between the mounting element and the optical source, the mounting element is in thermal contact with the optical source. In an aspect, a portion of the outlet passage is in physical contact with a mounting element supporting an optical source of an optical particle sensor of the present invention. In addition, the mounting element is provided in physical contact with the outlet passage and the flowing sample fluid within the outlet passage. This intimate connection enhances thermal exchange between the optical source and flowing sample fluid in the outlet passage via the mounting element.

Optical particle sensors of the present invention optionally have a plurality of outlet passage portions in thermal contact with the optical source. In an aspect, the sensor is capable of cooling a second heat-generating device with the outlet passage having a second portion in thermal contact with the heat-generating device. The outlet passage optionally cools two or more heat-generating devices in a serial flow path geometry. Alternatively, the outlet passages cools two or more heat-generating devices in a parallel flow-path geometry (e.g., simultaneously) by a junction that splits the flow-stream from a single outlet flow-path into two or more flow-paths. Any heat-generating device is amenable to cooling by the mechanisms and devices disclosed herein, including a heat-generating device selected from the group consisting of a power source, motor, pump, optical component, blowers, blower motor, regenerative blower, and fan.

In an aspect, the outlet passage portion in thermal contact with the optical source or with the mounting element is a plenum. Exhaust sample that exits the sample chamber enters the plenum. This flowing exhaust sample in the plenum has a temperature that is lower than the operating temperature of the optical source, such that flowing exhaust sample in the plenum is capable of thermally regulating the optical source. Accordingly, the plenum contains a volume of flowing sample fluid for cooling the optical source. In an embodiment, the plenum has a shape selected to maximize the surface area of the plenum in thermal contact with the optical source. Flowing exhaust sample in the plenum exits the plenum and is conveyed out of the optical particle sensor body. This flux of exhaust sample through the plenum provides the capability of continuous thermal management of the optical source, and any other components in thermal contact with the plenum.

In an aspect, the invention is further characterized by expressing flow-rate, fluid properties, and geometrical dimension in terms of a dimensionless constant, such as a Reynolds number (Re). In an embodiment, the flowing sample fluid in the plenum is turbulent or substantially turbulent. In an alternative embodiment, the flowing sample fluid in the plenum is laminar Flow is substantially turbulent for a plenum that has fluid mixing or turbulence at least in the region immediately surrounding the plenum face positioned closest to the optical source or the optical source mount. More specifically, the fluid sample within the plenum can have a Re of 2300 for turbulent flow. In an embodiment, the fluid sample within the plenum can have a Re of between about 2200 and 2900 for substantially turbulent or turbulent flow. In an embodiment, the fluid sample within the plenum can have a Re of about 2000 for laminar flow. In an aspect, any one or more of the physical or geometric parameters of pressure, temperature, flow rate, surface area in thermal contact shape and/or position are selected to provide adequate cooling of the optical light source.

Any of the sensors optionally have a plenum with at least one surface that corresponds to the optical source mount exterior surface. Such shared surface(s) assist in facilitating more efficient heat exchange between the optical source/ mount and the flowing sample fluid within the plenum. Preferably, the surface area of this plenum wall is relatively large to further increase heat exchange, corresponding to greater than about 10 times the surface area of an optical source that is a laser diode. In an aspect, the plenum surface that corresponds to the optical source mount exterior surface has a surface area greater than about 650 mm$^2$.

Plenums of systems and methods of the present invention optionally have a pair of orifices for introducing and removing flowing fluid sample to and from the plenum. Inlet tubing having a first end connected to the plenum inlet orifice and a second end connected to the sample chamber outlet facilitates introduction of fluid sample to the plenum. Alternatively, the inlet tubing may connect to the outlet passage at a position downstream of the sample chamber outlet. Outlet tubing having a first end connected to the plenum outlet orifice and a second end connected to an exhaust orifice facilitates removal of flowing fluid sample from the plenum and out of the sensor.

In an aspect, the temperature of the fluid sample at the plenum inlet orifice is about 5° C. to about 10° C. less than the optical source operating temperature.

Any of the sensors optionally have a plurality of plenums, wherein each plenum is in thermal contact with the optical source. This can be particularly useful for optical sources that have a tendency to generate excessive heat that must be dissipated. A plurality of plenums is also useful for optical source mounts having a plurality of exterior faces, wherein a plenum is paired with a mount face.

In an embodiment, the outlet passage portion in thermal contact with the optical source is a heat sink with an inlet heat sink orifice and outlet heat sink orifice. In this embodiment, the fluid sample at the inlet heat sink orifice has an inlet temperature, wherein the inlet temperature is less than the optical source operating temperature. Accordingly, the lower temperature of flowing sample fluid in the heat sink provides cooling of the optical source. In an aspect, the heat sink comprises one or more heat transfer passages. In an aspect, the heat transfer passage has a geometric shape selected from the group consisting of a spiral, fin, chamber, rectangular bore and circular bore.

In an embodiment, the invention has a plurality of heat transfer passages that are connected in a parallel, series, or parallel and series configuration to the inlet heat sink orifice and the outlet heat sink orifice. In this embodiment, flowing sample fluid is introduced and removed from each of the heat transfer passages such that the flowing sample fluid within the heat transfer passage is capable of conveying heat generated by the optical source. The "heated" sample fluid is transported to the exhaust outlet and removed from the sensor, thereby cooling the optical source. The portion in thermal contact with the optical source or mount is optionally described as having a horizontal surface footprint, with larger footprints providing the ability to dissipate more heat. In an aspect, the heat sink comprises tubing capable of transporting the sample fluid.

The magnitude of heat transfer is also affected by the separation distance of the heat generating element (e.g., an optical source) and the heat dissipating element (e.g., the flowing sample fluid within the portion of the outlet passage in thermal contact with the optical source). In an aspect, the outlet passage portion in thermal contact is separated from the optical source by a separation distance ranging up to about 2 cm.

Systems and methods of the present invention are designed to thermally manage optical sources in optical particle sensor devices by dissipating heat generated by the optical source. In an embodiment, the cooling mechanism is capable of dissipating or removing sufficient heat to maintain an about 100 mW or greater powered optical source at an operating temperature that is about 5° C. to 15° C. less than the operating temperature of an optical source in a sensor without a fluid sample exhaust cooling. "Conventional sensor" refers to a sensor that does not have a fluid sample exhaust cooling mechanism of the present invention.

In another aspect, the outlet passage is configured to have a cross-flow geometry relative to the optical source. "Cross-flow geometry" refers to a flow path that traverses from one side of the optical source to the corresponding opposite side of the optical source. For robust heat exchange, the flow path is optionally split so that substantially the entire surface area of the optical source is in good thermal contact with the flowstream, such as that depicted in FIG. 2E-2F, for example.

An alternative embodiment of the invention provides an airflow-cooled particle measuring device. The device has an optical source for generating electromagnetic radiation for detecting particles and an optical source mount for connecting the optical source to the particle counter. An airflow cavity transports air for cooling the optical source, wherein the airflow cavity is in thermal contact with the optical source. In an embodiment, the airflow cavity comprises a plurality of channels in the optical source mount. Alternatively, the airflow cavity is a shaped air plenum. In an aspect the airflow cavity is the volume space defined between the exterior surface of the optical source and the inward-facing surface(s) of the source mount. In another aspect, the airflow cavity comprises tubing in which airflow is constrained.

In an aspect, the transported air has a flow rate selected from a range of between about 0.5 cfm to about 1.5 cfm. In an aspect, the device further comprises means for forcing air through said airflow cavity. Means for forcing airflow through the cavity is known in the art, and includes fans, pumps, vacuum sources that are operably connected to the airflow cavity.

In an aspect, the invention is a method of cooling an optical source or a particle sensor. The method of cooling an optical source involves providing a particle sensor that has a sample chamber with an inlet orifice for receiving an input flow of at least a portion of fluid sample and an outlet orifice for conducting an exhaust flow fluid sample out of the sample chamber. An optical source is provided in optical communication with the sample chamber. An outlet passage is provided in fluid communication with the outlet orifice of the sample chamber for receiving the exhaust flow of the fluid sample from the sample chamber. The outlet passage has a portion in thermal contact with the optical source. Cooling occurs by flowing the fluid sample through the sample chamber and the outlet passage, thereby generating input flow of sample fluid and exhaust flow of sample fluid to provide thermal exchange between exhaust flow of sample fluid flowing through the outlet passage and the optical source. This thermal exchange results in optical source cooling. In an aspect, a portion of said exhaust flow is directed to provide cooling of another heat generating device, such as a blower motor, for example. In an aspect this cooling is in a parallel configuration wherein separate exhaust flow-streams achieve separate cooling of the optical device a second heat-generating device (referred herein as "simultaneous cooling"). Alternatively, a serial configuration flow-path provides for cooling of the optical source and the other heat-generating device(s) by a single flow-stream. In an aspect a total of two heat-generating devices (including the optical source) are cooled. In an aspect, three or more heat-generating devices are cooled.

The optical source is optionally connected to the particle counter by an optical source mount, and the outlet passage portion in thermal contact with the optical source is separated from an external surface of the mount by a distance less than about 20 mm. Any of the devices, sensors or methods of the present invention can have an optical source that is a laser diode.

In the context where it may be necessary to continuously analyze a given fluid sample, or repeat sample measurements on a given sample fluid volume, the method further comprises collecting the fluid sample from the outlet passage at an exhaust port and introducing at least a portion of the collected fluid sample to the inlet orifice of the sample chamber.

In the embodiment where the heat sink comprises passages, the passages optionally have a luminal area. In another embodiment, the exhaust flow through the outlet passage has a volumetric flow-rate selected from the range of about 1 cfm (28.3 L/min) to about 100 L/min.

In an embodiment, the invention is a method of cooling a particle sensor by providing an optical source in optical contact with a sample chamber and an airflow cavity in thermal contact with the optical source, wherein the airflow cavity is capable of facilitating airflow. This airflow dissipates heat build-up by the optical source, thereby cooling said particle sensor.

Any of the cooling methods may use any of the presently disclosed particle sensors. In an embodiment, the invention is a method of making a self-cooling particle sensor by providing an optical source in optical contact with a sample chamber and an outlet passage that collects at least a portion of sample fluid from the sample chamber. Configuring the outlet passage such that the sample fluid within the outlet passage establishes thermal contact with the optical source provides self-cooling of the particle sensor.

In an embodiment, the surface temperature of a surface in thermal contact with the outlet passage is preferably no greater than about 5° C. or about 2° C. above sample volume temperature. To avoid condensation on the surface in thermal contact, its temperature is maintained above the dewpoint temperature of air within the body of the particle counter.

In an embodiment, the outlet passage that is in thermal contact with a surface whose heat is being dissipated is a shaped heat sink or exchanger having a serpentine passage with outlet fluid sample flowing therethrough.

DETAILED DESCRIPTION OF THE INVENTION

Figure 1:
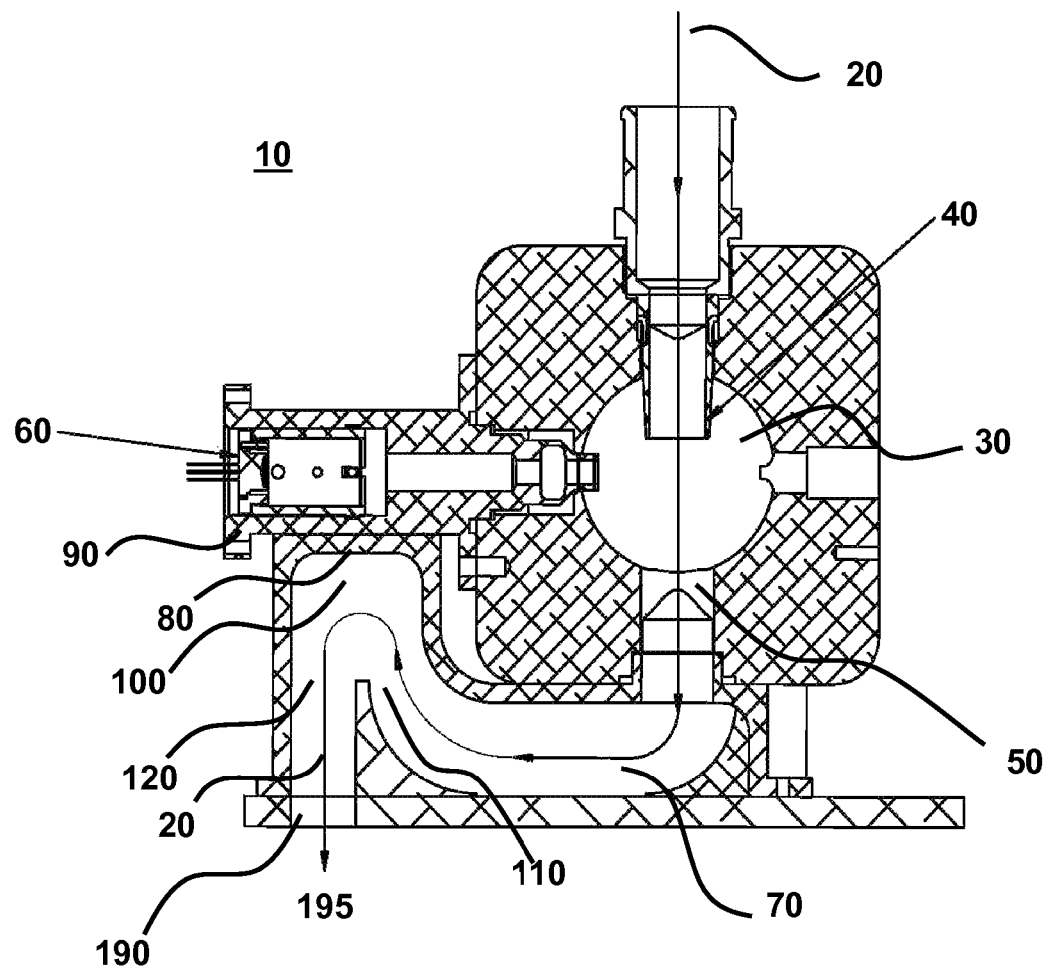
FIG. 1 is a schematic of a particle sensor having a plenum to facilitate cooling of an optical source.

"Particle sensor" refers to a device that is capable of providing information about particles suspended within a fluid. The fluid can be liquid or gas phase. The particles can be constrained or unconstrained within the fluid. Examples of particle information generated by such sensors include counts, concentration, size, size distribution, shape or other information generated by interaction of the optical source with the particle (e.g., fluorescent signal).

"Optical source" refers to a device or device component that is capable of delivering electromagnetic radiation to a sample. The term is not limited to visible radiation, such as by a visible light beam, but is used in a broad sense to include any electromagnetic radiation. The optical source may be embodied as a laser or laser array, such as a diode laser, diode laser array, diode laser pumped solid state laser, LEDs, LED arrays, gas phase laser, solid state laser, to name a few examples. "Optical communication" refers to an interaction (or lack of an interaction) between the output of the optical source and one or more particles in the fluid sample positioned within the sample chamber that provides useful and quantifiable information about the sample.

"Outlet passage" refers to a conduit that conveys fluid sample from the sample chamber for the purpose of cooling a heat-producing element such as an optical source. The optical passage may be connected directly or indirectly to the sample chamber. An example of a direct connection is an outlet passage that has one end attached to the sample chamber outlet orifice. An indirect connection includes connection to a sample fluid-containing location at a point downstream from the sample chamber. For example, the outlet passage can be connected to an intervening passage or tubing connected to the sample chamber. Any connection that provides "fluid communication" between the outlet passage and sample chamber can be used in the present invention. "Fluid communication" refers to fluid within the sample chamber that is capable of being conveyed to and through the outlet passage to provide cooling. In particular, cooling is provided by positioning a portion of the outlet passage with respect to a heat-generating device so that "thermal contact" is established between the two.

"Thermal contact" refers to one element being capable of affecting the operating or steady-state temperature of another element by removing heat from the element. In the present invention a cooling fluid, such as sample fluid that is within an outlet passage is capable of conducting heat from the optical source and out of the particle sensor and conveying "heated" sample fluid out of the particle sensor. Two elements in thermal contact facilitate "thermal exchange" from the element having a higher temperature to the element having a lower temperature, such as from an optical source to a sample fluid. Two elements in thermal contact need not be in direct physical contact. For example, the materials can be separated by a material, preferably by a material exhibiting high thermal conductivity, such as a metal (e.g., aluminum or copper), thermal grease or a thermally conductive pad. For example, the cooling sample fluid within the outlet passage is said to be in thermal contact with the optical source although the sample fluid is physically separated from the optical source by an optical source mount and optionally by other materials such as the outlet passage wall (for the embodiment where exhaust fluid is contained within walled passages such as tubing). Thermal contact may also refer to a fluid that is in direct physical contact with a heat-producing element, such as fluid (e.g., air) within a fluid (e.g., airflow) cavity that surrounds an optical device.

"Optical source mount" or "mounting element" refers to the manner in which one element (e.g., optical source) is positioned and held within the sensor. Mount is used broadly to refer to any structural element of the device, and particularly elements having high heat-conducting properties such as a metal. At least a portion of the material separating the outlet passage and surface in thermal contact is made of a material having good heat-transfer characteristics, e.g., metal, aluminum or copper. Optionally, the interior facing surface of the outlet passage is coated with a chemically-inert material to minimize chemical reaction of sample fluid within the outlet passage with a heat-conducting surface that may be less chemically-inert with the fluid sample.

The ability of the fluid sample within the outlet passage to provide cooling of a heat-producing source such as an optical source depends on a number of factors. One factor is the flow-rate and flow-characteristics of the fluid sample. Accordingly, the outlet passage is capable of transmitting flow of fluid sample at appropriate flow-rates, including user-selected flow-rates. "Transmitting flow" refers to the amount of sample fluid that is flowing into and correspondingly exiting, the outlet passage. This flow can be quantitatively expressed in any manner such as a volumetric flowrate, average fluid velocity, as well as incorporated into dimensionless variables such as a Reynolds number.

The Reynolds number (Re) is the ratio of inertial to viscous forces in a flowing system and is calculated by: $Re=\rho VD/\eta$, where $\rho$ is the fluid density, V is the average velocity, D is a characteristic length such as channel diameter, width or length, and $\eta$ the fluid viscosity. Re is useful in describing whether a fluid flow is turbulent or laminar. In general, a Re less than about 2000 is considered laminar, but the precise cut-off is variable depending on flow conditions, geometry and perturbations to the system. Because laminar flow tends not to mix (except by diffusion), in the heat exchange context of the present invention it is generally preferable that the fluid sample flow in the region where thermal contact and exchange is desired be substantially turbulent with Re, for example, greater than about 2000, 2500-4500, or about 3000-4000. Adequate mixing of fluid flow to ensure increased heat exchange can be further facilitated by incorporating baffles or other flow-disturbing elements within the outlet passage.

The pressure within the outlet passage is another parameter associated with heat exchange between the fluid sample within the outlet passage and the optical source. In general, especially for gas state fluids, higher pressures facilitate greater heat exchange. The "pressure difference" between the sample chamber and outlet passage refers to the difference between the average pressure within the sample chamber and the outlet passage. This pressure difference is generated by any means known in the art including a vacuum source or a fluid pump. Unless a pressure is specified for a specific location, the pressure refers to an average pressure within the component.

An outlet passage in "physical contact" with a mounting element refers to there being no intervening material between the fluid sample coolant and mount surface, except for an optional thin layer of chemically-inert material. For example, an outlet passage further comprising channels directly in the mounting element of a plenum having at least one surface that is the outer surface of the mounting element is said to be in physical contact with the mounting element.

A "plenum" refers to that portion of the outlet passage having a specially designed volume in which heat exchange is maximized. Preferably, a plenum has at least one surface corresponding to the optical source mount to provide maximum heat exchange between the optical source and the sample fluid within the plenum. This surface can be further shaped to contain a plurality of channels of different shapes and orientation to facilitate heat exchange. The plenum volume refers to the volume defined by the plenum walls and plenum inlet(s) and outlet(s).

"Heat sink" refers to a region of the outlet passage, including a separate component connected to the outlet passage, designed to enhance heat exchange. Such a heat sink provides an ability to more precisely tailor the passage geometry of cooling fluid flow compared to a plenum. In particular, the heat sink can have any number of individual heat exchangers such as a plurality of self-contained or inter-connected passages and/or chambers within the optical source mount. In contrast to a plenum, a heat sink can be entirely contained within a to-be-cooled material. The passages can be configured to be straight-lines, curved, serpentine or any combination thereof. Alternatively, the passages can comprise tubing that is not integrally contained within the mount.

Any of the elements in thermal contact can be described with a "thermal exchange surface footprint." This footprint refers to the surface area of the mount in physical contact with the cooling sample fluid. Accordingly, a plenum with a surface that corresponds to a smooth mount face has a smaller thermal exchange surface footprint than a plenum having channels (e.g., radiating fins) etched into the mount face.

"Operating temperature" refers to a steady state temperature an optical source would achieve during use. Accordingly, the operating temperature of an optical source without the cooling embodiment of the present invention is higher than the operating temperature of an optical source incorporated into a device of the present invention.

"Exhaust" or "exhaust sample fluid" refers to flowing sample fluid that has exited the sample chamber. The exhaust is used to cool a heat-producing element by ensuring that at least a portion of flowing exhaust is in thermal contact with the heat-producing element and capable of thermal exchange to cool the heat-producing element.

In addition to providing cooling of an optical source, the present invention is capable of cooling other elements that tend to generate heat, including but not limited to power supplies, pump motors, or fans, to name a few examples.

All references cited throughout this application, for example patent documents including issued or granted patents or equivalents; patent application publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated. All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art. Whenever a range is given, such as a temperature, size, pressure, Re, or time range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that, materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLE 1

Plenum-Cooled Particle Sensor

FIG. 1 is a schematic illustration of a particle sensor 10. Referring to FIG. 1, a fluid sample 20 is introduced to a sample chamber 30 at an inlet orifice 40. An optical source 60 illuminates fluid sample within chamber 30 and information is collected and analyzed to provide information about the status of fluid sample 20, as known in the art, such as scattering (forward and/or side), intensity, emission spectra, etc. Fluid sample flows out of the sample chamber 30 at an outlet orifice 50 and into outlet passage 70. Fluid sample exits the particle sensor 10 at an exhaust orifice or port 190. The general path of flowing fluid sample 20 is indicated by the arrow that transits the sample chamber 30 and outlet passage 70.

In this example, the outlet passage 70 further comprises a plenum 100 having a portion 80 in thermal contact with the optical source 60. In an embodiment, optical source 60 is positioned within the particle sensor 10 by a mounting element or optical source mount 90. In an embodiment, the outlet passage 70, and more particularly portion 80 of plenum 100 is in thermal contact with mounting element or mount 90.

Plenum 100 optionally has a plenum inlet orifice 110 and a plenum outlet orifice 120 for the introduction and exit of sample flow to and from plenum 100, respectively. Plenum 100 is shaped to have a volume and thermal exchange footprint that ensures maximum heat transfer from the optical source 60 and/or mounting element 90 to flowing sample fluid within plenum 100. Heat transferred to flowing sample fluid within plenum 100 is transported out of the sensor 10 by sample flow exhaust 195 comprising flowing sample volume from plenum 100 and out of the outlet passage 70 at exhaust orifice 190, thereby generally cooling particle sensor 10, and specifically optical source 60.

In an embodiment, the plenum 100 can be shaped and/or replaced by a heat sink chamber 200 having an inlet heat sink orifice 210 and an outlet heat sink orifice 220 to convey flowing fluid sample to facilitate cooling of the optical source 60, such as those illustrated in FIG. 2. The heat sink chamber optionally comprises one or more heat transfer passages 230 through the mounting element 90 to maximize heat transfer from the optical source 60 (FIG. 2E).

To control the flow-rate of fluid sample within the outlet passage 70, means for generating fluid flow is operably connected to outlet passage 70. Any means known in the art for generating fluid flow, including means having user-selected flow-rate capability, may be used, including but not limited to pumps, airflow pumps, centrifugal pumps, vacuum source, centripetal fans, blowers.

A plenum as part of a heat-exchange mechanism is advantageous because it can serve as part of the mounting element 90. Mount 90 assists in securing the optical source 60 to the other parts of the particle sensor 10. A mounting element that is a part of a plenum surface can reduce manufacturing complexity and cost. In addition, the plenum and/or outlet passage can be configured and positioned to cool other heat-generating areas within the particle sensor, such as pumps, motors, detectors or power supplies. A plenum that is physically connected to the mount element 90 refers to a mount that provides structural integrity and/or geometric constraint to the plenum 100, such as by defining a plenum surface. This embodiment also maximizes thermal contact and exchange by minimizing the separation distance between the mount 90 and plenum 100 as well as between the optical source 60 and plenum surface.

As understood in the art, heat dissipation and associated temperatures are numerically solvable for a variety of systems by solving the heat equation with one boundary condition corresponding to the temperature of the plenum surface in thermal contact with the mount. This temperature is affected by the flowing sample fluid coolant over the plenum surface and is, therefore, modeled by the flow equation to account for flow characteristics and heat convection. Another boundary condition is given by the operating temperature of the optical source. The partial differential equations arising from the geometry and conditions for a plenum-cooled optical source with a 1 cfm fluid sample at 20° C. flow rate through the plenum and a 30° C. optical source operating temperature have been numerically solved. In silico experiments demonstrate the portion of a plenum in thermal communication with an optical source provides significant cooling of the optical source. Two orthogonal slices through the center of the optical source are shown having a temperature distribution ranging from 19.85° C. to 28.85° C. The portion of the outlet passage in thermal contact with the optical source remains at a temperature of about 20-21° C., whereas the opposite side of the optical source from the portion in thermal contact has a temperature closer to 30° C. The model is for a 20° C. environment and 30° C. enclosure temperature with a 1 cfm flow rate, indicating the laser diode maintains a steady-state temperature of about 23° C. during operation. The cooling action of the flowing sample fluid results in a laser diode operating temperature of 23° C. This is significant cooling as empirical observations indicate that laser life approximately doubles for every 10° C. decrease in operating temperature. In addition, designs that do not provide the cooling mechanism of the present invention have an optical source operating temperature that is at least 3° C. to 5° C. above ambient temperature. The computational experiment presented herein provides useful information related to design parameters, including appropriate flow conditions (flow-rate, Re), geometry (e.g., thermal contact shape, separation distance) and resultant cooling temperatures for a variety of high-powered optical sources and ambient temperature conditions.

EXAMPLE 2

Self-Contained Heat Sink Connected to Outlet Orifice

Figure 5:
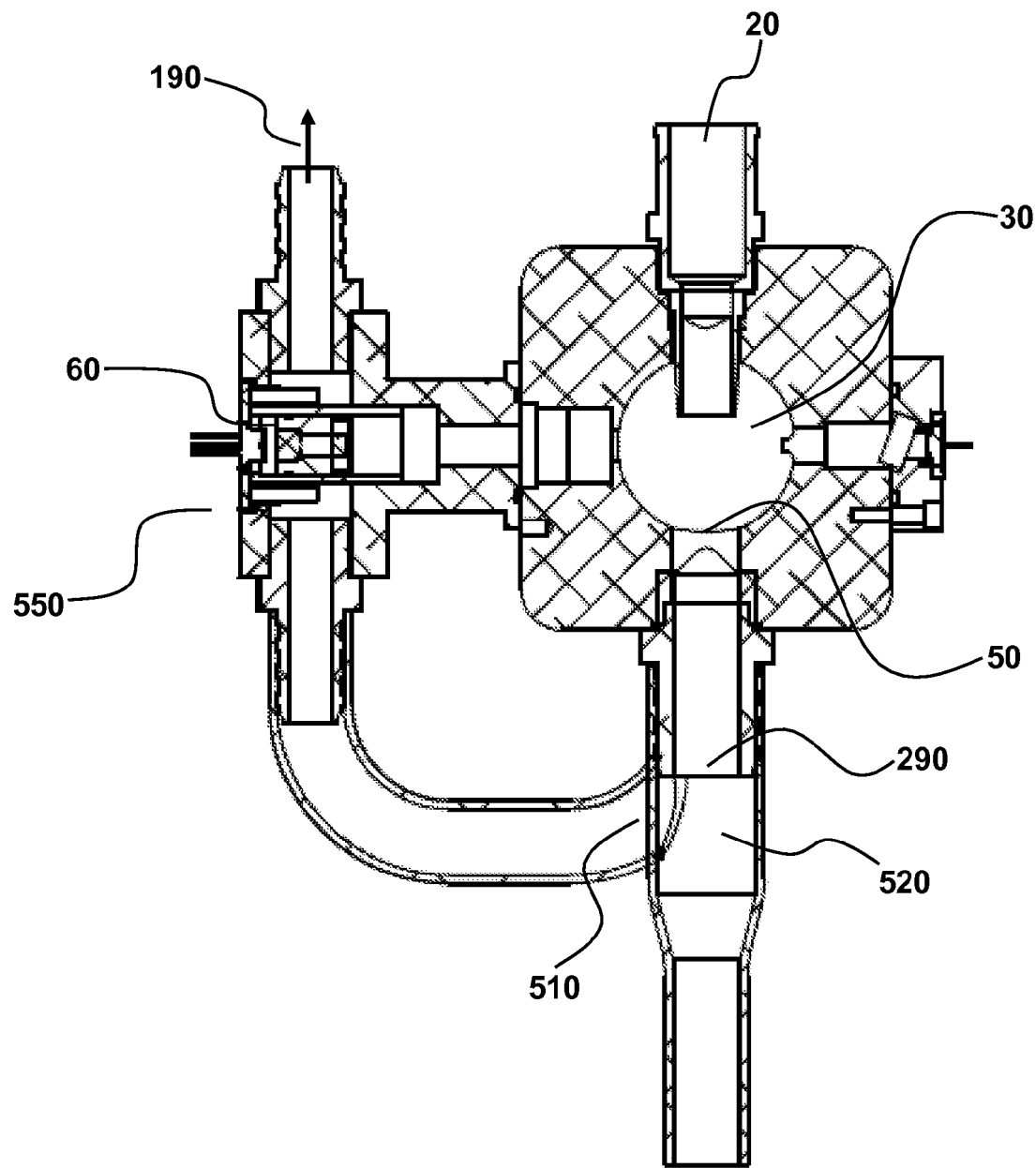
FIG. 5 illustrates a cross-flow sensor with split exhaust.
Figure 6:
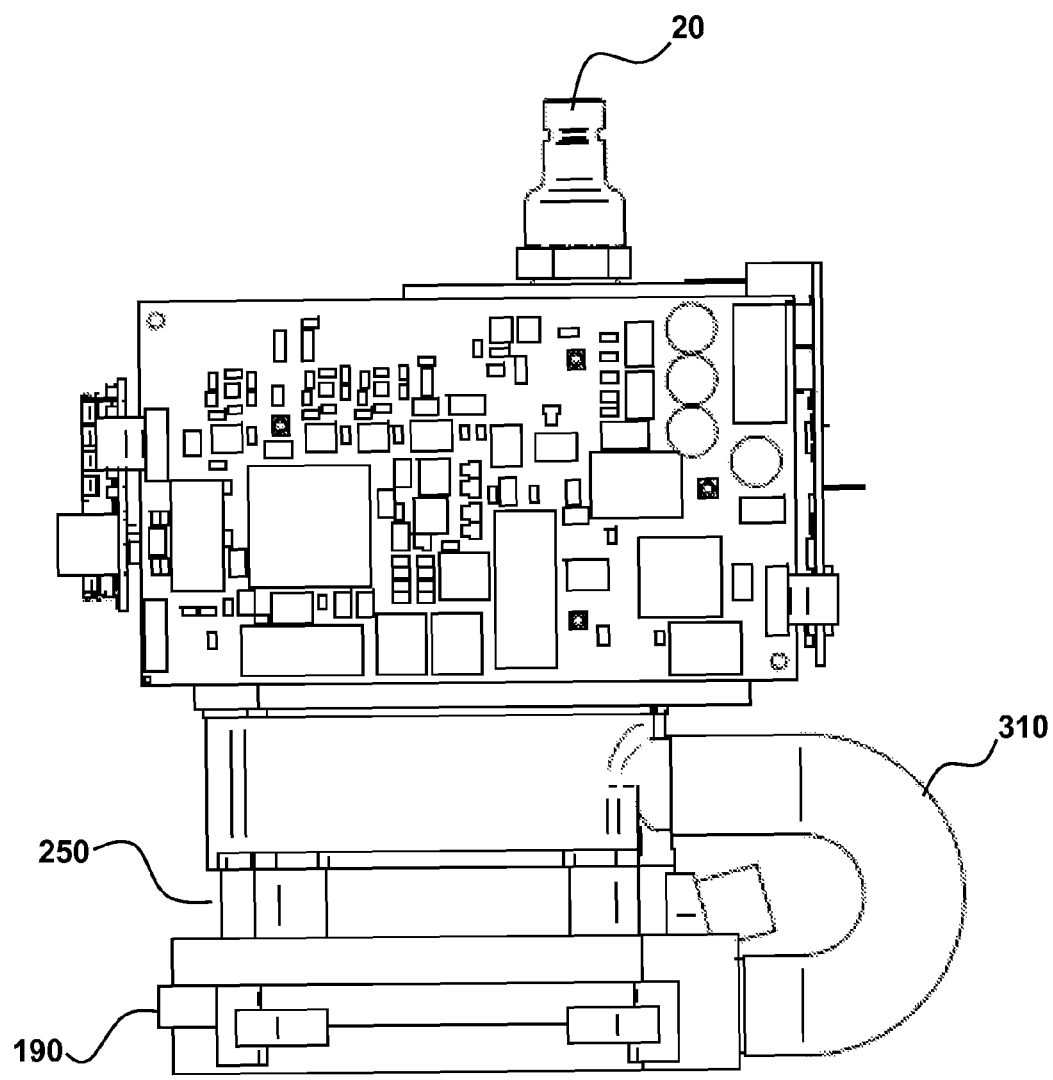
FIG. 6 is a side-view of a self-cooled sensor.
Figure 7:
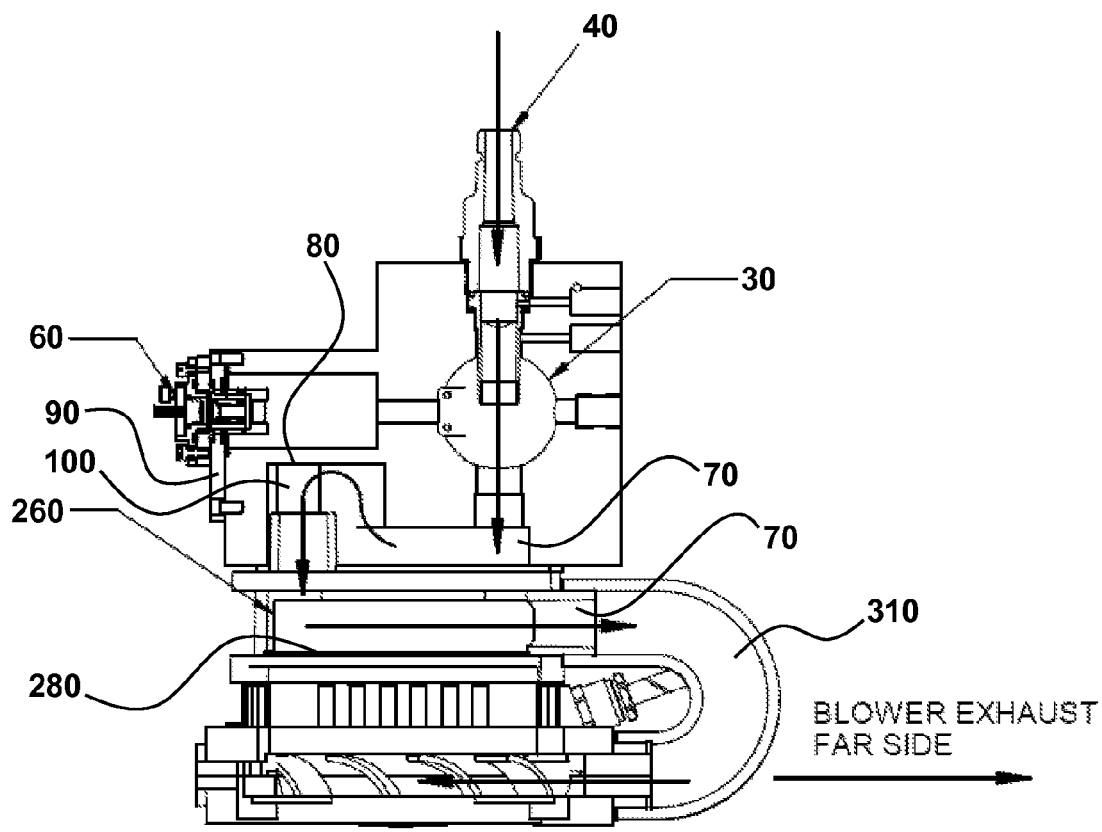
FIG. 7 is a selective cut providing a cross-section corresponding to each level of the flow-path (depicted as arrows within flow-path) of the sensor in FIG. 6. The cut in the central portion exposes a motor cover. The lower portion shows the vanes of the blower as they are exposed.
Figure 8:
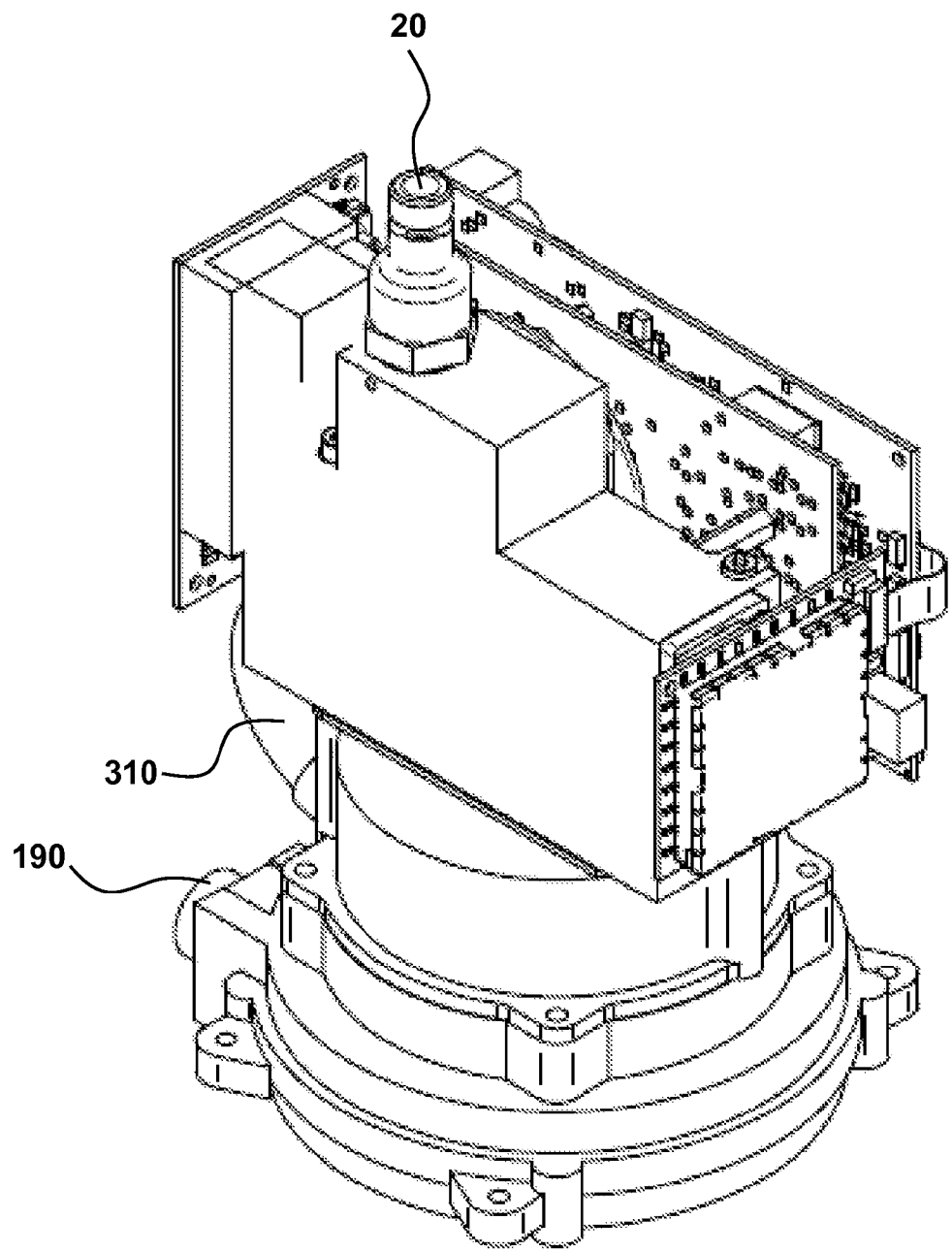
FIG. 8 is a front perspective view of the self-cooled sensor of FIG. 6 showing the laser module.
Figure 9:
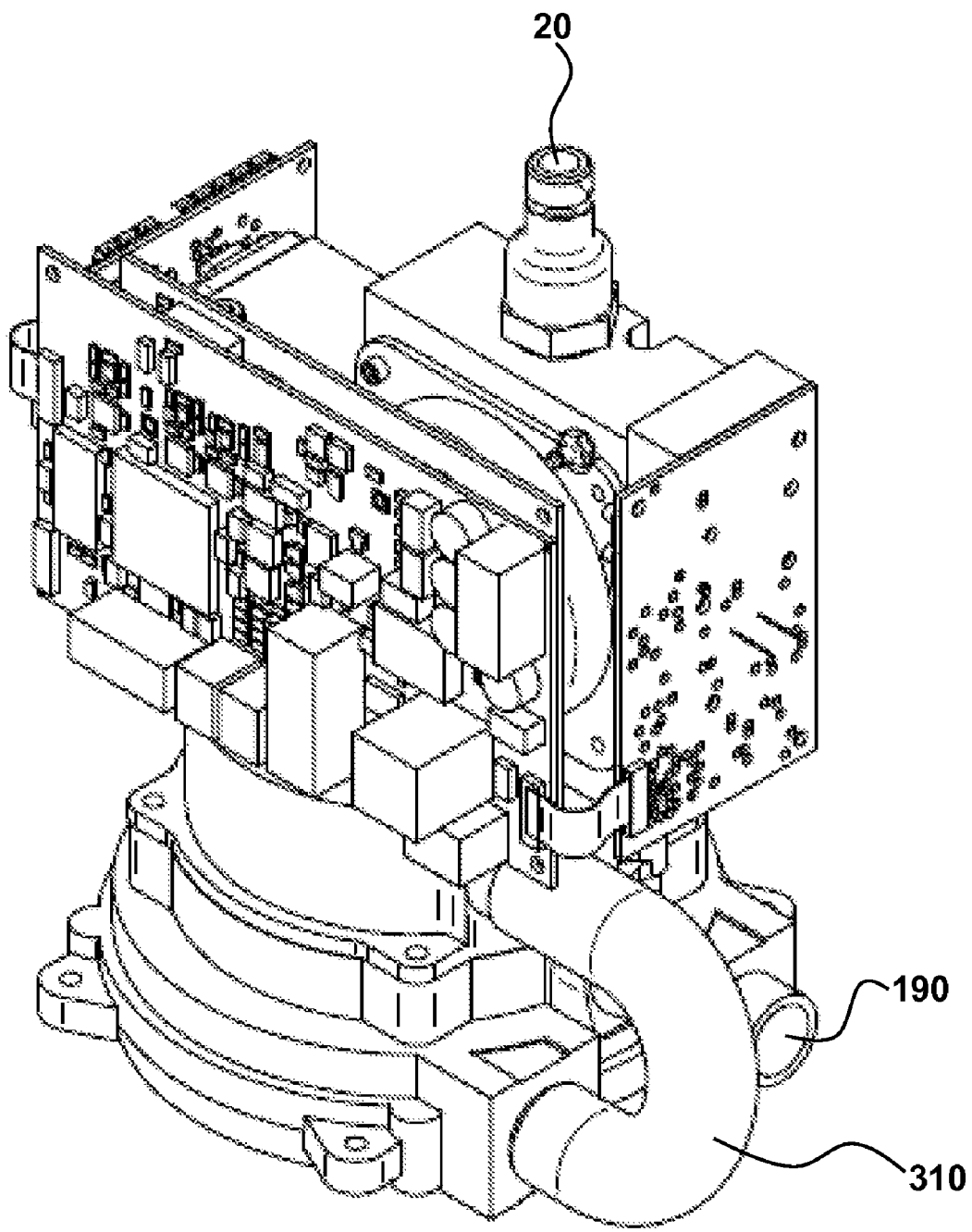
FIG. 9 is a rear perspective view of the self-cooled sensor of FIG. 6 showing the blower entry and exhaust ports.
Figure 10:
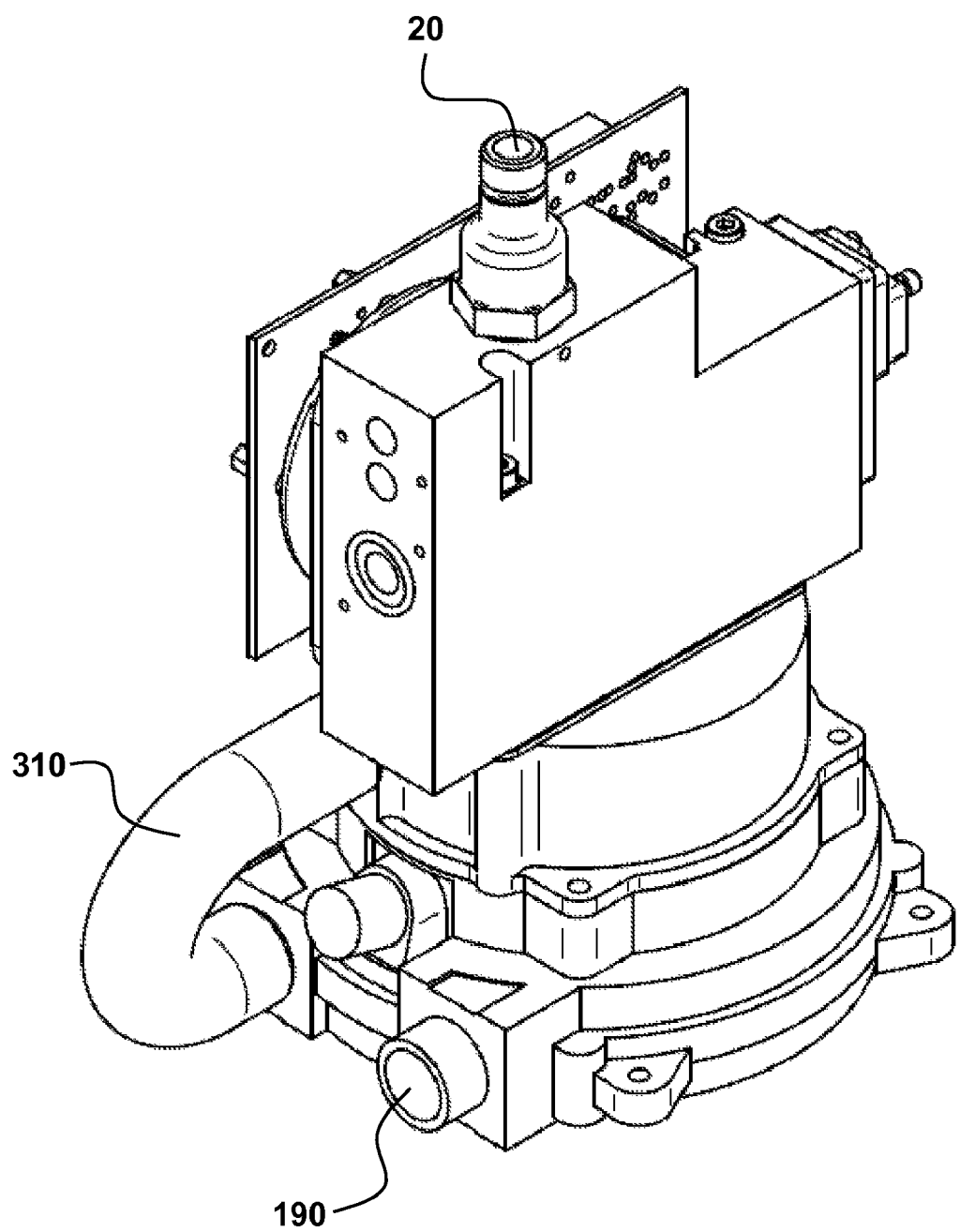
FIG. 10 is a side perspective view of the self-cooled sensor of FIG. 6.

In an embodiment, a mounting element 90 with integral heat sink 200 provides cooling, (see, for example, FIGS. 2 and 5). A heat sink conduit 205 that provides sample fluid 20 to the heat sink 200 is connected to the sample chamber outlet orifice 50, the exhaust orifice 190, or to an outlet passage location between the outlet orifice 50 and exhaust orifice 190. To transport fluid sample to the heat sink, the heat sink passage is operably connected to the means for generating fluid flow, such as vacuum source or pump. In an aspect, the heat sink conduit comprises tubing, including flexible tubing, connected at one end for receiving sample fluid, such as to chamber outlet orifice 50, outlet passage 70 or exhaust orifice/port 190 and at the other end to inlet heat sink orifice 210 for introducing the fluid sample to the heat sink.

Figure 2A:
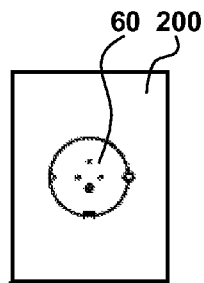
FIG. 2 illustrates various heat sinks positioned relative to an optical source. A End view of source and heat sink. B Side view. C. End view of illustrating various heat passages in a heat sink that is part of a mount for optical source. D Side view of optical source illustrating heat source having a fin geometry. E Top view of a cross-flow geometry of sample fluid cooling optical source with a plurality of heat transfer passages overlaying an optical source. F is a cross-section of optical source with a heat sink flow passage in intimate contact for maximizing heat exchange between optical source and sample fluid within the heat sink flow passage.
Figure 2B:
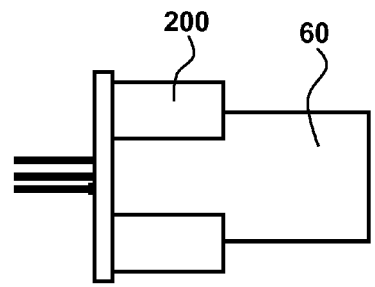
Figure 2C:
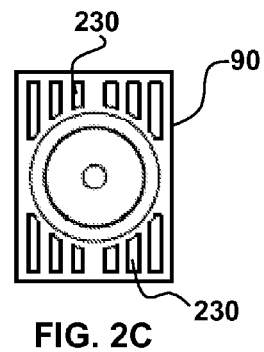
Figure 2D:
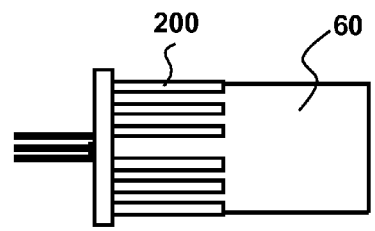
Figure 2E:
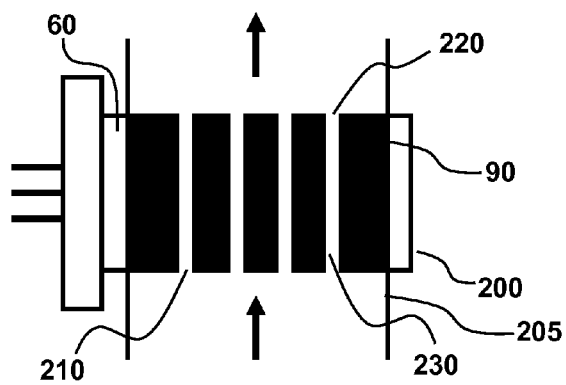
Figure 2F:
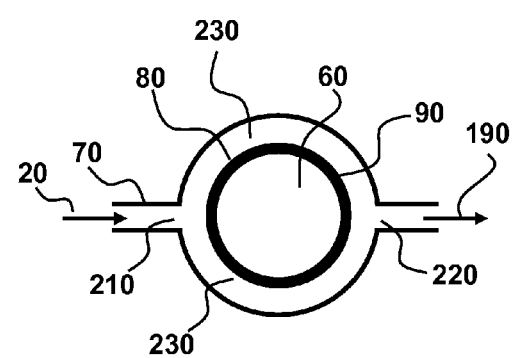

The heat sink optionally comprises one or more heat sink transfer passages 230 within the mounting element 90 through which fluid sample flows for cooling the optical source 60 (see FIG. 2E). In an aspect, the heat sink passages are configured to provide high surface areas for thermal exchange with the mount 90. For example, passages having a relatively large depth into the mount compared to the width (e.g., width less than 50%, 30% or 10% of depth) facilitate heat exchange without unduly impacting the mount structural integrity. Such geometry is referred to as a "fin" structure. Alternatively, the fin structure is oriented in the opposite direction to facilitate heat exchange (e.g., depth less than 50%, 30% or 10% of height); this orientation is referred to as a "heat sink chamber." The heat sink can comprise any geometry such as a plurality of these structures, including multiple fin and/or chamber structures having different orientations.

Any of the heat exchange surfaces can be tailored to the specific optical source mount 90 geometry. For example, a multiple-sided mount can have multiple heat sinks (or plenums) to provide increased heat transfer from each of the mount sides. A mount with curved sides can have heat sinks, passages or plenums 230 with a similar curved orientation (see FIG. 2F).

The laser assembly heat sinks of the present invention do not constrain the pump to any particular location within the product housing. For example, a heat sink conduit comprising tubing facilitates transfer of sample fluid coolant from any location to the device that is to be cooled in a relatively simple and cost-effective manner. The downstream end of the heat sink, e.g., the outlet heat sink orifice itself can be an exhaust port or can also have a passage or tubing to transport the sample volume to an appropriate location or connection within the particle sensor.

EXAMPLE 3

Airflow Cavity Within Mounting Assembly

An alternative cooling process relates to an airflow cavity positioned between the optical source 60 and optical source mount 90. In this aspect, air is routed into and out of the cavity using either tubing or a shaped air plenum. Although this aspect eliminates one thermal interface (e.g., the air coolant is in direct contact with the optical source), there is added complexity and cost that is minimized for the embodiments that use the sample fluid itself as the coolant. In this aspect, air is forced into the cavity by any means known in the art such as a fan or pump.

EXAMPLE 4

Multiple Device Cooling

Figure 3:
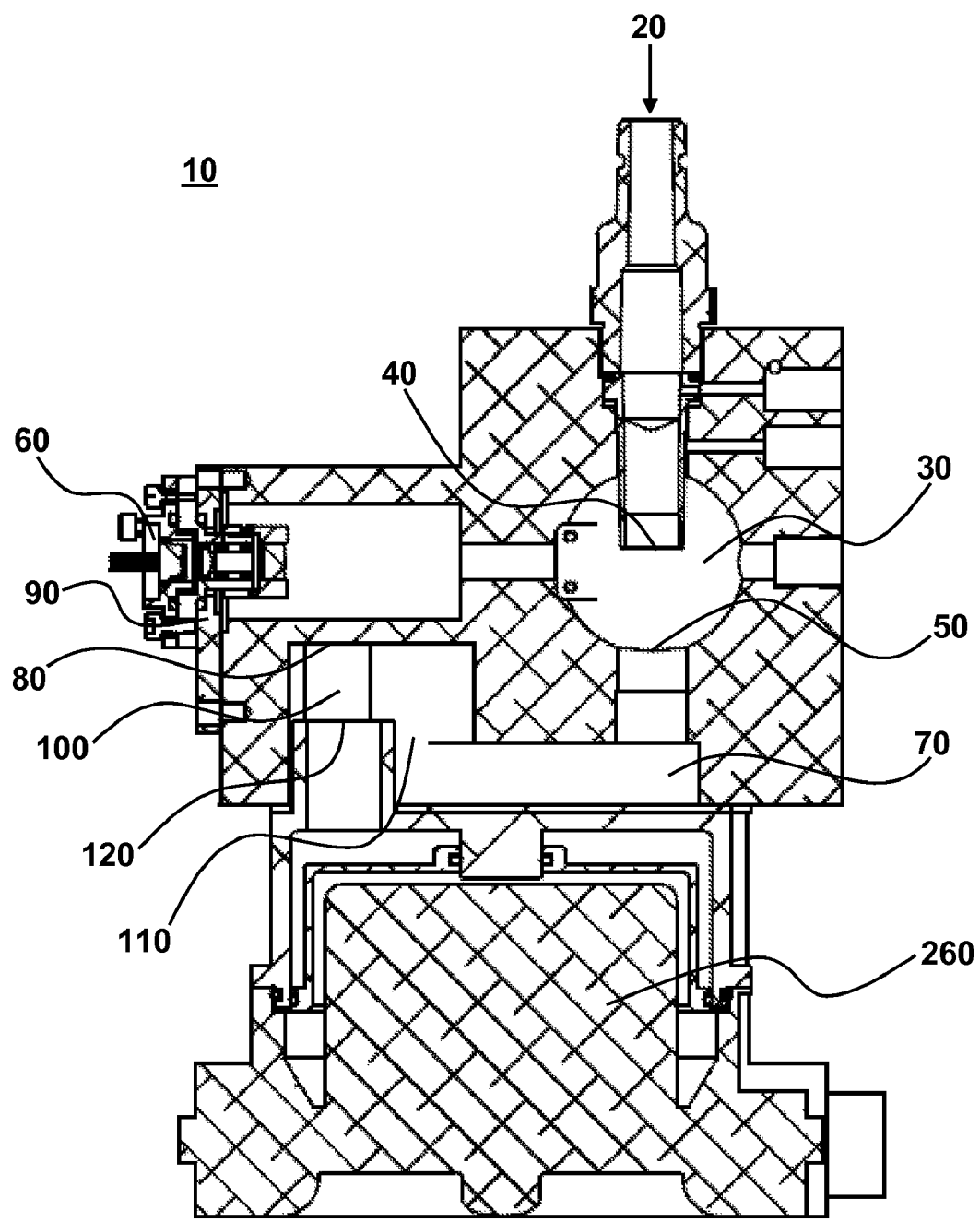
FIG. 3 is a sensor that cools an optical source and a second heat-generating device.

Provided herein are various configurations for cooling a plurality of heat-generating devices within the sensor, and for finer control of flows and flows into optional multiple flowpaths. FIG. 3 illustrates a geometrical configuration of the outlet passage 70 for cooling an optical source 60 and then a heat-generating device 260, such as a blower motor. In this example all the sample fluid collected at outlet orifice 50 flows along outlet passage 70, plenum 100 for cooling optical source 60 and then exits plenum 100 at plenum outlet 120 for subsequent cooling of heat-generating device 260.

Figure 4:
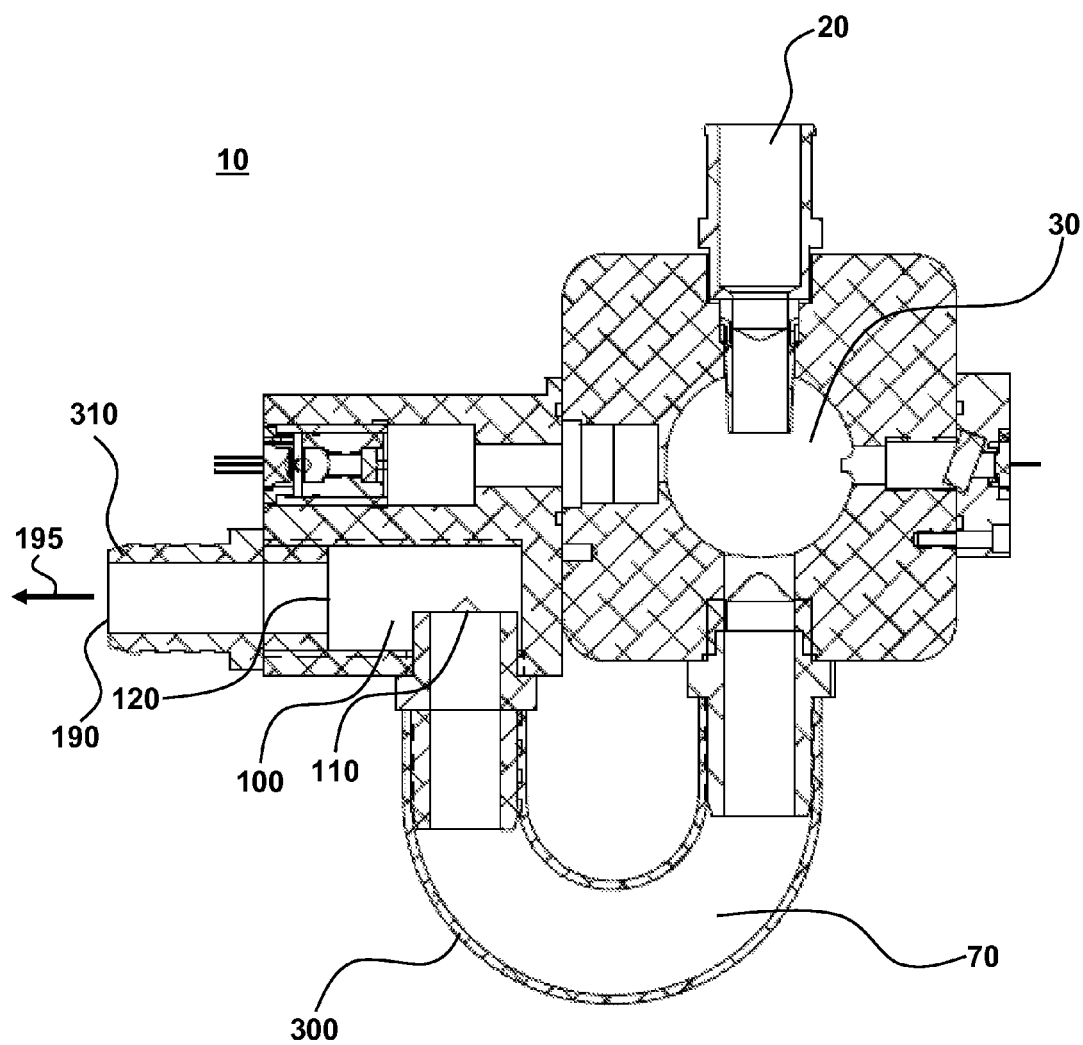
FIG. 4 illustrates a sensor having tubing for conveying sample fluid.

FIG. 4 provides another embodiment where outlet passage 70 further comprises a portion of inlet tubing 300 that introduces sample fluid to plenum 100 at plenum inlet orifice 110. Outlet, such as outlet conduit or tubing 310 removes sample fluid from the plenum outlet orifice 120, thereby conveying sample from plenum 100 to exhaust orifice 190, such that heated exhaust sample fluid 195 is removed from sensor 10. In this example, optional plurality of plenums (corresponding to 100 and a plenum positioned within tubing 300) can provide plurality of cooling tailored to specific sensor locations, as necessary.

Another flowpath geometry for cooling multiple devices in the sensor is provided in FIG. 5. In this embodiment, outlet passage 70 comprises a junction 290 that splits outlet passage 70 into a first flowpath 510 and a second flowpath 520. FIG. 5 further illustrates a cross-flow geometry 550 of that portion of outlet passage 70 (e.g., flowpath 510) that cools optical source 60. Examples of heat sinks for use in a "cross-flow" geometry include, but are not limited to, those shown in FIGS. 2E and 2F In an embodiment, flowpath 520 is exhausted to environment. In an embodiment, flowpath 520 is directed to cool a heat-generating device. In an aspect, the relative amounts of flow between flowpath 510 and 520 are regulated as needed, such as providing higher flows to the path in need of greater heat dissipation, or for decreasing flow when heat generation conditions are lower. This regulation can be automated as known in the art such as by temperature sensors operably connected to valves or flow-regulators that control flow in each of 510 and 520.

Various views of one embodiment of a self-cooled sensor are provided in FIGS. 6-10, showing various other features such as related electronics, laser modules, blowers, etc.

REFERENCES

Particle counters, sensors and related optical sources and configurations are known in the art and in which the present invention may be incorporated, include but are not limited to U.S. Pat. Nos. 7,088,447, 7,088,446, 7,030,980, 6,945,090, 6,903,818, 6,859,277, 6,709,311, 6,690,696, 6,615,679, 6,275,290, 6,246,474, 6,167,107, 6,091,494, 5,903,338, 5,861,950, 5,805,281, 5,751,422, 5,671,046, 5,493,123, 5,459,569, 5,282,151, 5,134,622, 5,029,335, 4,893,932, 4,893,928, 4,798,465, 4,740,988, 4,728,190, 4,636,075, 4,594,715, 4,571,079, 4,027,162, 4,011,459, 3,941,982, U.S. Pub. No. 2006/0038998. These references are hereby incorporated by reference in their entireties, as though individually incorporated by reference, to the extent each reference is not inconsistent with the disclosure in this application.

I claim:

1. A particle sensor for sensing particles in a fluid sample, said sensor comprising:
   a. a sample chamber having an inlet orifice for receiving a flow of said fluid sample and an outlet orifice for conducting said fluid sample out of said sample chamber;
   b. an optical source provided in optical communication with said sample chamber; and
   c. an outlet passage in fluid communication with said outlet orifice for receiving at least a portion of said flow of fluid sample from said sample chamber; said outlet passage having a portion in thermal contact with said optical source; wherein thermal exchange between said flow of sample fluid in said outlet passage and said optical source is capable of cooling said optical source.

2. The sensor of claim 1, wherein said optical source is a laser having a power consumption that is equal to or greater than 100 mW.

3. The sensor of claim 1, wherein said optical source has an operating temperature and said fluid sample has a fluid sample temperature, and said thermal exchange between said flow of sample fluid in said outlet passage and said optical source is capable of maintaining said optical source operating temperature within about 5 degrees Celsius of said fluid sample temperature.

4. The sensor of claim 3, wherein said fluid sample at said sample chamber outlet has a temperature selected from a range of between about 20° C. and about 30° C.

5. The sensor of claim 1, wherein the temperature of said flowing sample fluid in said outlet passage is between about 3° C. to 8° C. less than said optical source operating temperature.

6. The sensor of claim 1 wherein said outlet passage is capable of transmitting said flow of fluid sample at flow rates selected from the range of greater than and equal to 25 L/min and less than or equal to 100 L/minute.

7. The sensor of claim 1 having a chamber pressure in said sample chamber and an outlet pressure in said outlet passage, wherein said chamber pressure and said outlet pressure are within about 10% of each other.

8. The sensor of claim 1 further comprising a mounting element that supports said optical source, wherein a portion of said outlet passage is in physical contact with said mounting element.

9. The sensor of claim 1, wherein said outlet passage further comprises a second portion in thermal contact with a heat-generating device.

10. The sensor of claim 9, wherein said outlet passage further comprises a junction, wherein said junction divides said flow of fluid sample into a plurality of flowpaths for cooling a plurality of said heat-generating device.

11. The sensor of claim 10, wherein said junction divides said flow of fluid sample into two flowpaths, wherein a first flowpath is capable of cooling said optical source, and a second flowpath is capable of cooling a heat-generating device.

12. The sensor of claim 11, wherein said heat-generating device is a blower motor.

13. The sensor of claim 9, wherein the heat-generating device is selected from the group consisting of a power source, motor, pump, optical component, regenerative blower and fan.

14. The apparatus of claim 1, wherein said outlet passage portion in thermal contact with said optical source comprises a plenum.

15. The sensor of claim 14, wherein said plenum has a surface area in thermal contact with said optical source that is greater than about 650 mm$^2$.

16. The sensor of claim 14, wherein said fluid sample within said plenum has a Reynolds number selected from a range of 2200 and 2900.

17. The sensor of claim 14 having an optical source mount for connecting said optical source to said sensor, wherein said plenum is connected to said optical source mount.

18. The sensor of claim 17, wherein said optical source mount has an exterior surface and said plenum has at least one surface that corresponds to said optical source mount exterior surface.

19. The sensor of claim 18, wherein said plenum surface that corresponds to said optical source mount exterior surface has a surface area selected from a range of between about 650 mm$^2$ and 1500 mm$^2$.

20. The sensor of claim 14 comprising a plurality of plenums, wherein each plenum is in thermal contact with said optical source.

21. The sensor of claim 1, wherein said outlet passage portion in thermal contact with said optical source is separated from said optical source by a separation distance that is less than about 2 cm.

22. The sensor of claim 1, wherein said thermal contact portion is capable of sustaining an the optical source at a temperature that is between about 5° C. to about 15° C. less than a corresponding optical source temperature in a conventional sensor.

23. The sensor of claim 1, wherein said outlet passage in thermal contact with said optical source is configured in a cross-flow geometry relative to said optical source.

24. A method for cooling an optical source of a particle sensor comprising:
 a. providing said particle sensor comprising:
  i. a sample chamber having an inlet orifice for receiving an input flow of said fluid sample and an outlet orifice for conducting an exhaust flow said fluid sample out of said sample chamber; and
  ii. an optical source provided in optical communication with said sample chamber; and
 b. providing an outlet passage in fluid communication with said outlet orifice of said sample chamber for receiving at least a portion of said exhaust flow of said fluid sample from said sample chamber;
 said outlet passage having a portion in thermal contact with said optical source; and
 c. flowing said fluid sample through said sample chamber and said outlet passage, thereby generating said input flow of sample fluid and said exhaust flow of sample fluid;
wherein thermal exchange between said at least a portion of exhaust flow of sample fluid flowing through said outlet passage and said optical source cools said optical source.

25. The method of claim 24, wherein said optical source is connected to said particle counter by an optical source mount, and said outlet passage portion in thermal contact with said optical source is separated from an external surface of said mount by a distance less than about 2 cm.

26. The method of claim 25 further comprising:
 a. collecting said fluid sample from said outlet passage at an exhaust port; and
 b. introducing at least a portion of said fluid sample collected at said exhaust port to said sample chamber.

27. The method of claim 25, wherein said outlet passage in thermal contact with said optical source comprises a heat sink.

28. The method of claim 27, wherein said heat sink comprises conduits attached to a plurality of heat transfer passages in said optical source mount for providing said exhaust flow to said heat transfer passages.

29. The method of claim 24, wherein said outlet passage in thermal contact with said optical source comprises a plenum.

30. The method of claim 29, wherein said plenum comprises a plenum surface in thermal contact with said optical source, said surface having a surface area that is greater than 650 mm$^2$.

31. The method of claim 24 further comprising:
 a. directing a portion of said exhaust flow to a heat-generating device to provide cooling of said optical source and said heat-generating device.

32. A method of making a self-cooling particle sensor comprising:
 a. providing an optical source in optical contact with a sample chamber;
 b. providing an outlet passage that collects at least a portion of sample fluid from said sample chamber; and
 c. configuring said outlet passage such that said sample fluid within said outlet passage thermally contacts said optical source to provide self-cooling of the particle sensor.

33. A particle sensor for sensing particles in a fluid sample, said sensor comprising:
 a. a sample chamber having an inlet orifice for receiving a flow of said fluid sample and an outlet orifice for conducting said fluid sample out of said sample chamber;
 b. an optical source provided in optical communication with said sample chamber; and
 c. an outlet passage in fluid communication with said outlet orifice for receiving at least a portion of said flow of fluid sample from said sample chamber; said outlet passage having a portion in thermal contact with said optical source; wherein thermal exchange between said flow of sample fluid in said outlet passage and said optical source is capable of cooling said optical source
 wherein said outlet passage portion in thermal contact with said optical source comprises a plenum, said plenum comprising:
  a plenum inlet orifice for receiving flow of said fluid sample;
  a plenum outlet orifice for conducting said fluid sample out of said plenum;
  inlet tubing having a first end connected to said plenum inlet orifice and a second end connected to said sample chamber outlet or said outlet passage for introducing sample fluid to said plenum inlet orifice; and outlet tubing having a first end connected to said plenum outlet orifice and a second end connected to an exhaust orifice for transporting fluid sample out of said sensor.

34. The sensor of claim 33 having an optical source operating temperature, wherein said fluid sample at said plenum inlet orifice has a temperature that is selected from about 5° C. to about 10° C. less than said optical source operating temperature.

35. The sensor of claim 33 wherein said optical source is a laser having a power consumption that is equal to or greater than 100 mW.

36. The sensor of claim 33 wherein said optical source has an operating temperature and said fluid sample has a fluid sample temperature, and said thermal exchange between said flow of sample fluid in said outlet passage and said optical source is capable of maintaining said optical source operating temperature within about 5 degrees Celsius of said fluid sample temperature.

37. The sensor of claim 33 wherein said outlet passage is capable of transmitting said flow of fluid sample at flow rates selected from the range of greater than and equal to 25 L/min and less than or equal to 100 L/minute.

38. The sensor of claim 33, wherein said plenum has a surface area in thermal contact with said optical source that is greater than about 650 mm$^2$.

39. The sensor of claim 33, wherein said fluid sample within said plenum has a Reynolds number selected from a range of 2200 and 2900.

40. The sensor of claim 33, further comprising an optical source mount for connecting said optical source to said sensor, wherein said plenum is connected to said optical source mount.

41. The sensor of claim 40, wherein said optical source mount has an exterior surface and said plenum has at least one surface that corresponds to said optical source mount exterior surface.

42. The sensor of claim 41, wherein said plenum surface that corresponds to said optical source mount exterior surface has a surface area selected from a range of between about 650 mm$^2$ and 1500 mm$^2$.

43. A particle sensor for sensing particles in a fluid sample, said sensor comprising:
   a. a sample chamber having an inlet orifice for receiving a flow of said fluid sample and an outlet orifice for conducting said fluid sample out of said sample chamber;
   b. an optical source provided in optical communication with said sample chamber; and
   c. an outlet passage in fluid communication with said outlet orifice for receiving at least a portion of said flow of fluid sample from said sample chamber; said outlet passage having a portion in thermal contact with said optical source; wherein thermal exchange between said flow of sample fluid in said outlet passage and said optical source is capable of cooling said optical source.

wherein the particle sensor has an optical source operating temperature, wherein said outlet passage portion in thermal contact with said optical source comprises a heat sink having an inlet heat sink orifice and outlet heat sink orifice, said fluid sample at said inlet heat sink orifice having an inlet temperature, wherein said inlet temperature is less than said optical source operating temperature.

44. The sensor of claim 43, wherein said heat sink comprises one or more heat transfer passages.

45. The sensor of claim 44, wherein said heat transfer passage has a geometric shape selected from the group consisting of a serpentine, spiral, fin, chamber, rectangular bore and circular bore.

46. The sensor of claim 44, comprising a plurality of heat transfer passages that are connected in a parallel configuration to said inlet heat sink orifice and said outlet heat sink orifice, thereby introducing and removing flowing fluid sample from each of said heat transfer passages; wherein said flowing sample fluid within said heat transfer passages are capable of conveying heat generated by the optical source to said exhaust outlet thereby cooling said optical source.

* * * * *